(12) United States Patent
Kim et al.

(10) Patent No.: US 8,977,360 B2
(45) Date of Patent: Mar. 10, 2015

(54) NEUROSTIMULATION SYSTEM WITH ON-EFFECTOR PROGRAMMER CONTROL

(75) Inventors: Chester Kim, Lynnwood, WA (US); Mun Pook Lui, Northridge, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 185 days.

(21) Appl. No.: 13/469,990

(22) Filed: May 11, 2012

(65) Prior Publication Data

US 2012/0290041 A1 Nov. 15, 2012

Related U.S. Application Data

(60) Provisional application No. 61/486,141, filed on May 13, 2011.

(51) Int. Cl.
*A61N 1/00* (2006.01)
*A61N 1/36* (2006.01)
*A61N 1/372* (2006.01)

(52) U.S. Cl.
CPC ........ *A61N 1/36071* (2013.01); *A61N 1/37247* (2013.01); *A61N 1/36157* (2013.01); *A61N 1/36185* (2013.01)
USPC ............................................ 607/30; 600/523

(58) Field of Classification Search
CPC ............................ A61N 1/37247; A61B 5/044
USPC ............................ 607/30–32, 59, 46; 600/523
See application file for complete search history.

(56) References Cited

U.S. PATENT DOCUMENTS

| | | | |
|---|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |
| 7,035,690 B2 | 4/2006 | Goetz |
| 7,650,184 B2 | 1/2010 | Walter |
| 7,987,000 B2 | 7/2011 | Moffitt et al. |
| 8,019,439 B2 | 9/2011 | Kuzma et al. |
| 2007/0150036 A1 | 6/2007 | Anderson |
| 2007/0168004 A1 | 7/2007 | Walter |
| 2007/0168007 A1 | 7/2007 | Kuzma et al. |

(Continued)

OTHER PUBLICATIONS

PCT International Search Report for PCT/US2012/037601, Applicant: Boston Scientific Neuromodulation Corporation, Form PCT/ISA/210 and 220, dated Dec. 5, 2012 (4pages).

(Continued)

*Primary Examiner* — Scott Getzow
(74) *Attorney, Agent, or Firm* — Schwegman Lundberg & Woessner, P.A.

(57) ABSTRACT

An external control device for use with a programmable implantable medical device coupled to an operative element. The external control device comprises a user interface comprising a control element and a display screen configured for displaying a graphical representation of the operative element. The external control device further comprises control circuitry configured for prompting the display screen to superimpose a graphical programmer control over the graphical representation of the operative element when the control element is actuated, and modifying an operational parameter for the operative element in response to actuation of the graphical programmer control. The external control device further comprises output circuitry configured for transmitting the modified operational parameter to the programmable implantable medical device.

19 Claims, 9 Drawing Sheets

(56) References Cited

U.S. PATENT DOCUMENTS

| | | |
|---|---|---|
| 2007/0203546 A1 | 8/2007 | Stone et al. |
| 2008/0163097 A1 | 7/2008 | Goetz et al. |
| 2008/0183256 A1 | 7/2008 | Keacher |
| 2010/0010566 A1 | 1/2010 | Thacker et al. |
| 2010/0057162 A1 | 3/2010 | Moffitt et al. |
| 2010/0121409 A1 | 5/2010 | Kothandaraman et al. |

OTHER PUBLICATIONS

PCT Written Opinion of the International Search Authority for PCT/US2012/037601, Applicant: Boston Scientific Neuromodulation Corporation, Form PCT/ISA/237, dated Dec. 5, 2012 (5pages).

PCT International Preliminary Report on Patentability (Chapter I of the Patent Cooperation Treaty) for PCT/US2012/037601, Applicant: Boston Scientific Neuromodulation Corporation, Form PCT/IB/326 and 373, dated Nov. 28, 2013 (7pages).

NEUROSTIMULATION SYSTEM WITH ON-EFFECTOR PROGRAMMER CONTROL

RELATED APPLICATION DATA

The present application claims the benefit under 35 U.S.C. §119 to U.S. provisional patent application Ser. No. 61/486,141, filed May 13, 2011. The foregoing application is hereby incorporated by reference into the present application in its entirety.

FIELD OF THE INVENTION

The present inventions relate to medical programmers, and in particular, to control devices for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device in the form of a remote control to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, a remote control can be used to instruct the neurostimulator to generate electrical stimulation pulses in accordance with the selected stimulation parameters. Typically, the stimulation parameters programmed into the neurostimulator can be adjusted by manipulating controls on the remote control to modify the electrical stimulation provided by the neurostimulator system to the patient. Thus, in accordance with the stimulation parameters programmed by the remote control, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. Once a polarity and the amplitude (either as an absolute or a percentage) for the current or voltage on an active electrode is selected in a typical computerized programming system, the polarity and amplitude value may be displayed on a display screen in association with this electrode to the user.

A programming user interface may include graphical programmer controls that are displayed on a conventional display screen or a digitizer display screen (e.g., a touchscreen). Typically, such graphical programmer controls are displayed in fixed positions relative to the display screen. However, with respect to stimulation parameters that are specific to each electrode (e.g., polarity and fractionalized current value), this traditional approach tends to confuse the user in terms of the relationship between the programmed stimulation parameters and the specific electrode to be programmed.

It may, thus, be desirable to provide a more intuitive use interface that associates a graphical programmer control in direct association with each displayed electrode for selecting the polarity and/or fractionalized current value for the respective electrode. However, due to the limited space on the display screen, as well as the close spacing between the displayed electrodes, it is difficult to associate a fully functional programmer control with each electrode without obscuring one or more of the other displayed electrodes, which problem is only worsened as the number of electrodes to be programmed increases (e.g., when the user interface must support sixteen or even thirty-two electrodes) and the display becomes more crowded as a result.

There, thus, remains a need to graphically associate a programmer control with an electrode in a spatially efficient manner.

SUMMARY OF THE INVENTION

In accordance with the present inventions, an external control device for use with a programmable implantable medical device coupled to an operative element is provided. The external control device comprises a user interface comprising a control element and a display screen configured for displaying a graphical representation of the operative element. In one embodiment, the control element is a graphical control element, which may be the graphical representation of the operative element.

The external control device further comprises control circuitry configured for prompting the display screen to superimpose a graphical programmer control over a graphical representation of the operative element when the control element is actuated. In one embodiment, the graphical control element occupies more area on the display screen than does the graphical representation of the operative element. In another embodiment, the graphical control element surrounds the graphical representation of the operative element.

The control circuitry is further configured for modifying an operational parameter for the operative element in response to actuation of the graphical programmer control. The external control device further comprises output circuitry (e.g., telemetry circuitry) configured for transmitting the modified operational parameter to the programmable implantable medical device. The external control device may further comprise a case containing the user interface, control circuitry, and output circuitry.

In one embodiment, the operative element is an end effector, such as an electrode, the implantable medical device is a neurostimulation device, and the operational parameter is a stimulation parameter.

In this case, the graphical programmer control may comprise at least one stimulation amplitude control element, the stimulation parameter may comprise a stimulation amplitude value (e.g., a fractionalized current value) for the electrode, and the control circuitry may be configured for modifying the stimulation amplitude value in response to actuation of the stimulation amplitude control element(s). The stimulation amplitude control element(s) may comprise an up arrow control element and a down arrow control element, in which case, the control circuitry may be configured for increasing the stimulation amplitude value in response to actuation of the up arrow control element, and for decreasing the stimulation amplitude value in response to actuation of the down arrow control element.

The graphical programmer control may also comprise at least one polarity control element, the stimulation parameter may comprise a polarity for the electrode, and the control circuitry may be configured for modifying the polarity in response to actuation of the at least one polarity control element. The polarity control element(s) may comprise a positive polarity control element and a negative polarity control element, in which case, the control circuitry may be configured for setting the polarity of the electrode to a positive polarity in response to actuation of the positive polarity control element, and for setting the polarity of the electrode to a negative polarity in response to actuation of the negative polarity control element.

In an optional embodiment, the user interface further comprises a display element incorporated within the graphical programmer control, in which case, the control circuitry may be further configured for prompting the display element to display a status of the modified operational element. If the implantable medical device is further coupled to other operative elements, the display screen may be configured for displaying graphical representations of the plurality of operative elements, in which case, the graphical programmer control preferably does not obscure any of the graphical representations of the other operative elements and/or any programming information displayed in association with the other operative elements.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. The patent or application file contains at least one drawing executed in color. Copies of this patent or patent application publication with color drawing(s) will be provided by the Office upon request and payment of the necessary fee. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
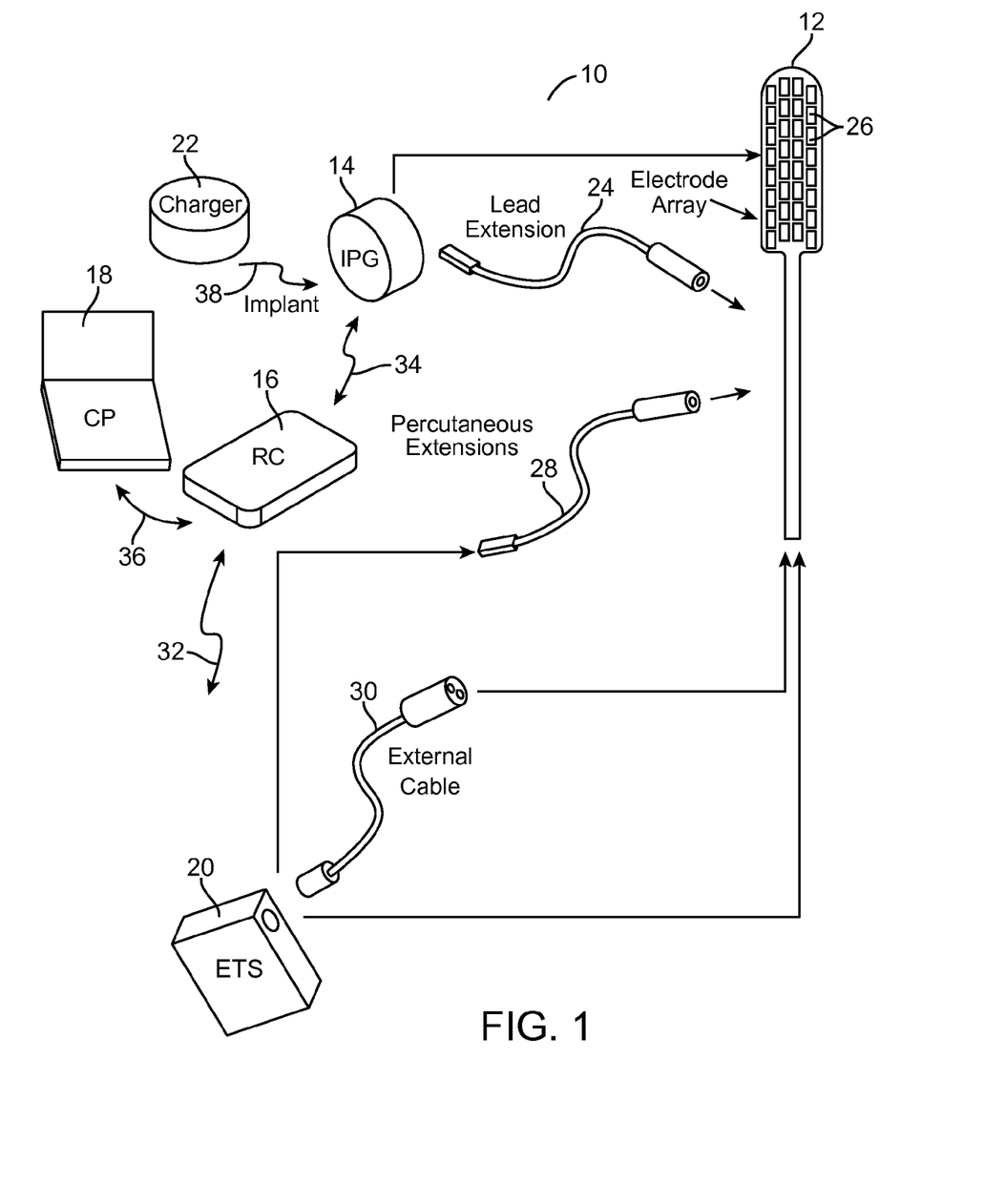
FIG. 1 is a plan view of a Spinal cord Stimulation (SCS) system constructed in accordance with one embodiment of the present inventions.

Turning first to FIG. 1, an exemplary SCS system 10 generally comprises at least one implantable neurostimulation lead 12, an implantable pulse generator (IPG) 14, an external remote control RC 16, a Clinician's Programmer (CP) 18, an External Trial Stimulator (ETS) 20, and an external charger 22.

The IPG 14 is physically connected via one or more lead extensions 24 to the neurostimulation lead 12, which carries a plurality of electrodes 26 arranged in an array. The neurostimulation lead 12 is illustrated as a surgical paddle lead in FIG. 1, although as will be described in further detail below, one or more percutaneous leads can be used in place of the surgical paddle lead 12. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
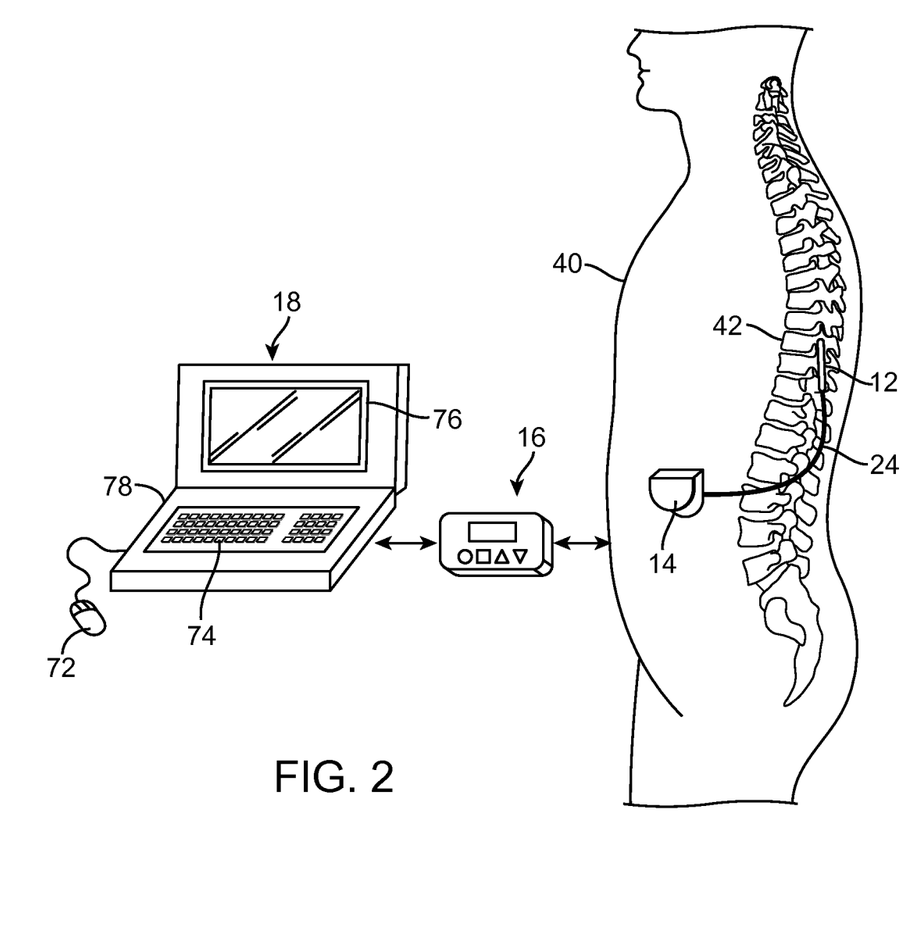
FIG. 2 is a perspective view of the arrangement of the SCS system of FIG. 1 with respect to a patient.

As shown in FIG. 2, the electrode lead 12 is implanted within the spinal column 42 of a patient 40. The preferred placement of the electrode lead 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
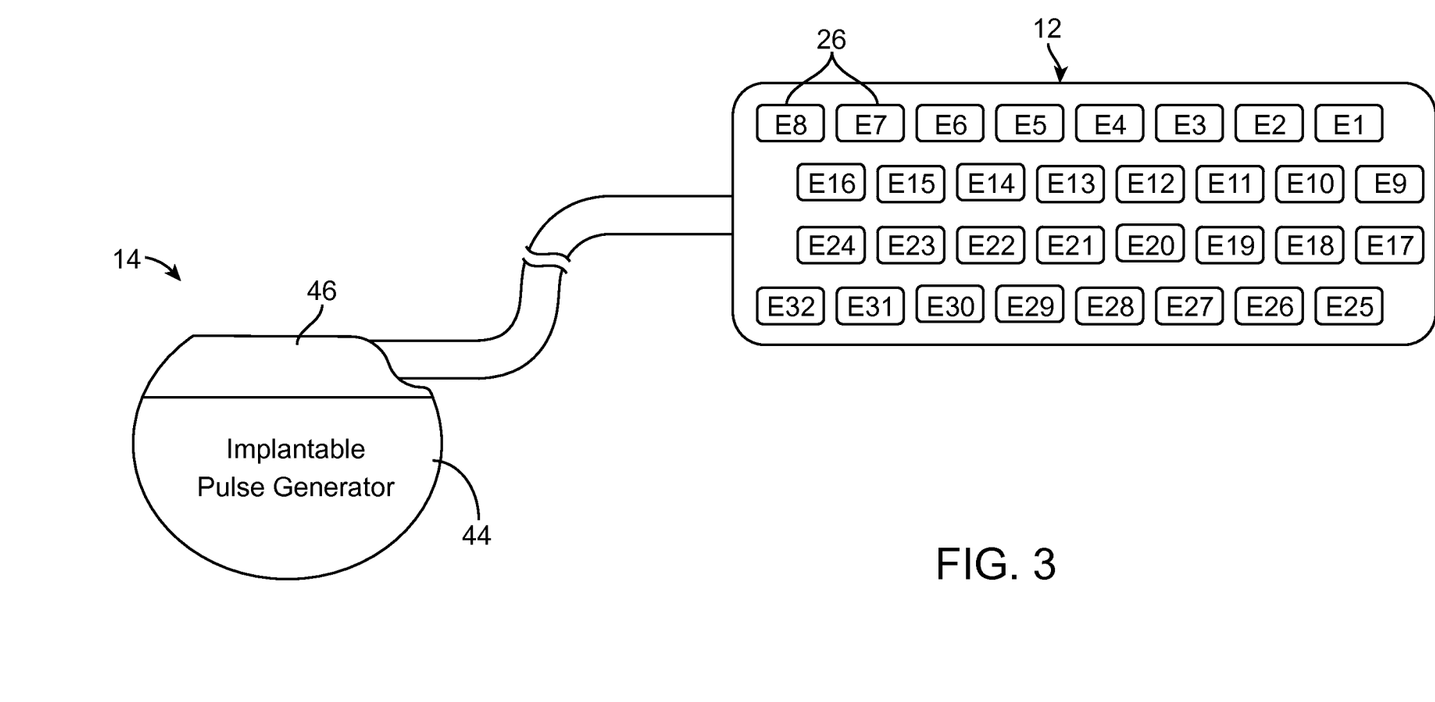
FIG. 3 is a profile view of an implantable pulse generator (IPG) and a surgical paddle neurostimulation lead used in the SCS system of FIG. 1.

Referring to FIG. 3, the IPG 14 comprises an outer case 44 for housing the electronic and other components (described in further detail below), and a connector 46 to which the proximal end of the neurostimulation lead 12 mates in a manner that electrically couples the electrodes 26 to the internal electronics (described in further detail below) within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

In the embodiment illustrated in FIG. 3, the neurostimulation lead 12 takes the form of a surgical paddle lead 12 on which the electrodes 26 (in this case, electrodes E1-E32) are carried. The electrodes 26 are arranged in a two-dimensional array in four columns along the axis of the neurostimulation lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," and U.S. patent application Ser. No. 12/204,094, entitled "Multiple Tunable Central Cathodes on a Paddle for Increased Medial-Lateral and Rostro-Caudal Flexibility via Current Steering, the disclosures of which are expressly incorporated herein by reference.

Figure 4:
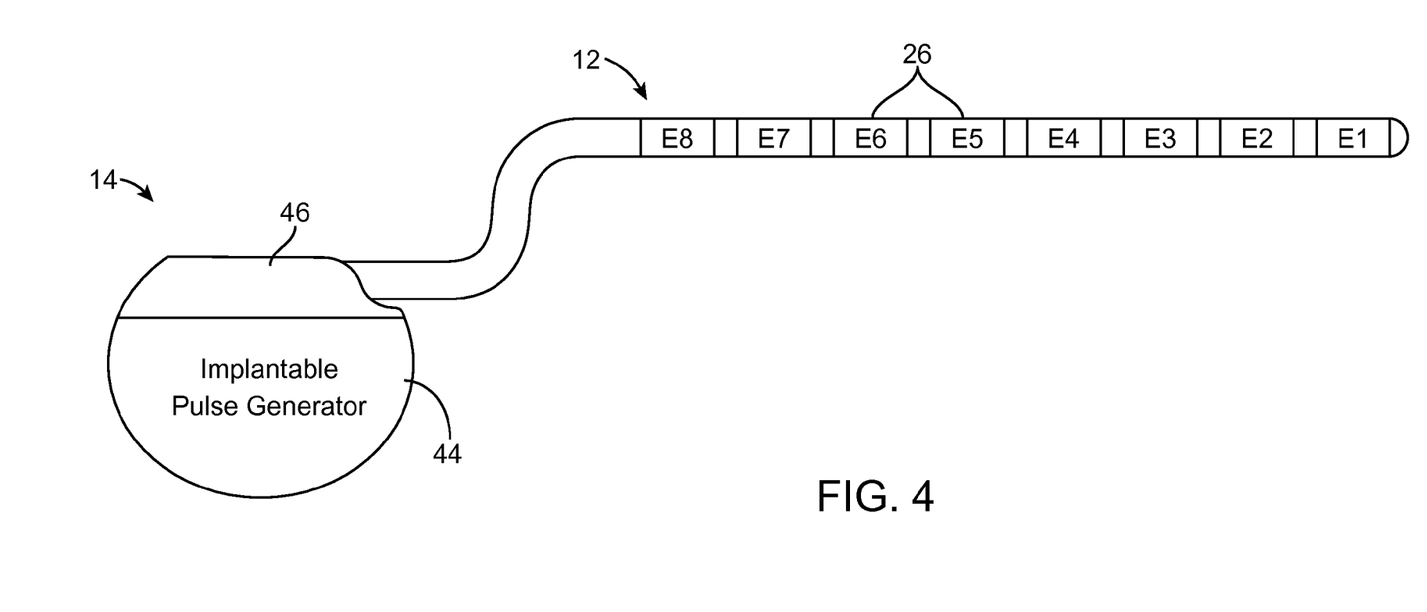
FIG. 4 is a profile view of an implantable pulse generator (IPG) and a percutaneous neurostimulation lead used in the SCS system of FIG. 1.

In an alternative embodiment illustrated in FIG. 4, the neurostimulation lead 12 takes the form of a percutaneous stimulation lead on which the electrodes 26 (in this case, electrodes E1-E8) are disposed as ring electrodes. Although only one percutaneous stimulation lead 12 is shown, multiple percutaneous stimulation leads (e.g., two), can be used with the SCS system 10. The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation phase and an anodic (positive) recharge phase that is generated after the stimulation phase to prevent direct current charge transfer through the tissue, thereby avoiding electrode degradation and cell trauma. That is, charge is delivered through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
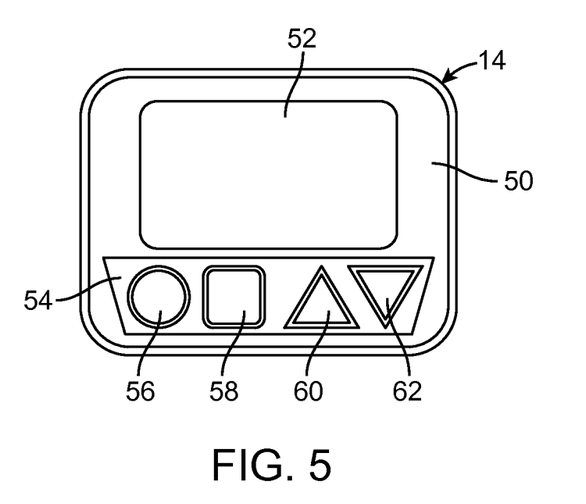
FIG. 5 is front view of a remote control (RC) used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
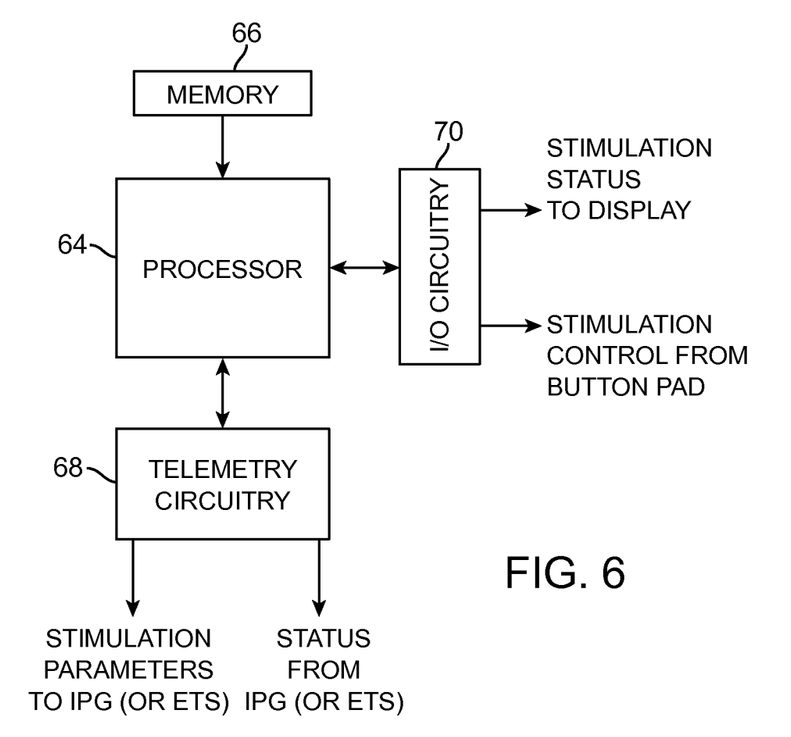
FIG. 6 is a block diagram of the internal components of the RC of FIG. 5.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 5). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74. In the illustrated embodiment, the monitor 76 is a conventional screen. Alternatively, instead of being conventional, the monitor 76 may be a digitizer screen, such as touchscreen (not shown), that may be used in conjunction with an active or passive digitizer stylus/finger touch.

Figure 7:
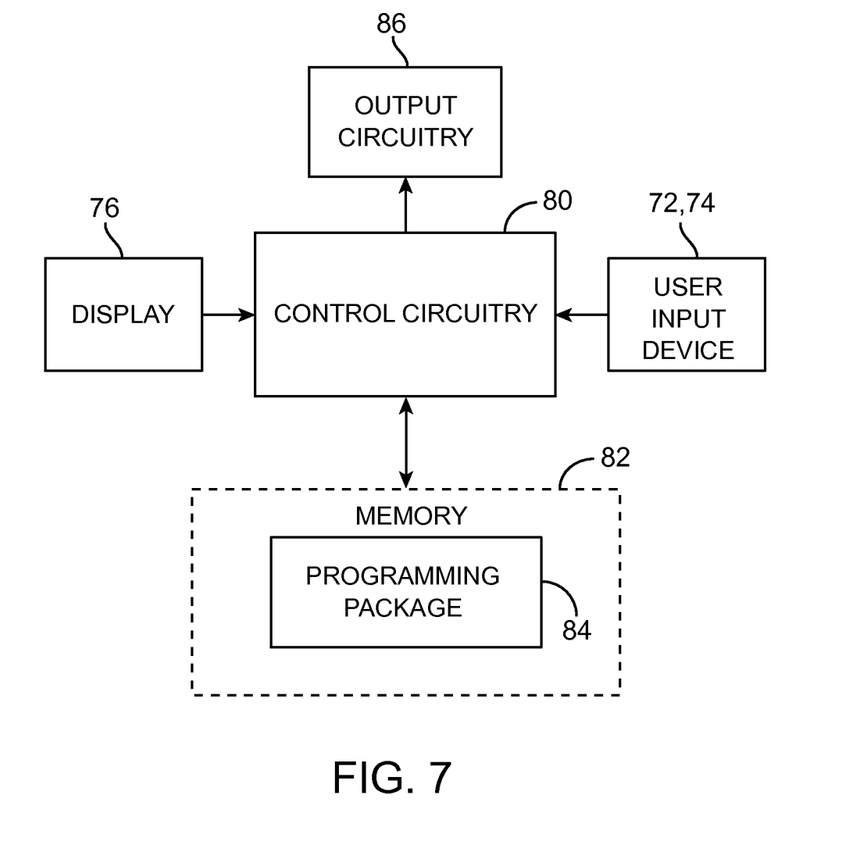
FIG. 7 is a block diagram of the internal components of a clinician's programmer (CP) used in the SCS system of FIG. 1.

As shown in FIG. 7, the CP 18 further includes a control circuitry 80 (e.g., a central processor unit (CPU)) and memory 82 that stores a stimulation programming package 84, which can be executed by the control circuitry 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the control circuitry 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 86 provides a more intuitive user interface that allows a user to individually program each electrode 26 without obscuring information associated with the other ones of the displayed electrodes 26.

In particular, and with reference to FIGS. 8a and 8b, an exemplary programming screen 100 generated by the CP 16 to allow a user to program the IPG 14 will now be described. The programming screen 100 includes various control elements described below that can be actuated to perform various control functions.

A pointing element may be placed on any of the control elements to perform the actuation event. As described above, in the case of a digitizer touch screen, the pointing element will be an actual pointing element (e.g., a finger or active or passive stylus) that can be used to physically tap the screen above the respective graphical control element or otherwise brought into proximity with respect to the graphical control element. In the case of a conventional screen, the pointing element will be a virtual pointing element (e.g., a cursor) that can be used to graphically click on the respective control element. In response to actuation of any of these control elements, the control circuitry 80 performs the designated function or functions corresponding to the actuated control element described below.

The programming screen 100 comprises a stimulation on/off control 102 that can be alternately actuated to initiate or cease the delivery of electrical stimulation energy from the IPG 14. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in Hertz (Hz)), and a pulse amplitude adjustment control 108 (expressed in milliamperes (mA)). Each control includes a first arrow that can be actuated to decrease the value of the respective stimulation parameter and a second arrow that can be actuated to increase the value of the respective stimulation parameter. The programming screen 100 also includes a multipolar/monopolar stimulation selection control 110, which includes check boxes that can be alternately actuated by the user to selectively provide multipolar or monopolar stimulation. The programming screen 100 also includes an electrode combination control 112 having arrows that can be actuated by the user to select one of multiple stored or present electrode combinations. For example, in electrode combination control 112, three different electrode combinations 1-3 are shown. Each of the electrode combinations 1-3 can be created using various ones of the control elements.

The programming screen 100 also includes a set of axial steering control elements 116 and a set of transverse steering control elements 118. In the illustrated embodiments, the control elements 116, 118, as well as the other control elements discussed herein, are implemented as a graphical icon that can be clicked with a mouse or touched with a finger in the case of a touchscreen.

When any of the axial steering control elements 116 is actuated, control signals are generated in response to which stimulation parameter sets designed to axially displace the locus of the electrical stimulation field (and thus, the volume of activation (VOA)) relative to the axis of the lead 12 are generated. Likewise, when any of the transverse steering control elements 118 is actuated, control signals are generated in response to which stimulation parameter sets designed to transversely displace the locus of the electrical stimulation field (and thus, the VOA) relative to the axis of the lead 12 are generated.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the plurality of stimulation parameter sets are generated. The output telemetry circuitry 86 is configured for transmitting these stimulation parameters sets to the IPG 14. Preferably, the control signals that are generated in response to the actuation of the control elements 116, 118 or the alternative control elements are directional, meaning that the locus of the electrical stimulation field will be displaced in a defined direction in response to a continual actuation of a single control element irrespective of the current position of the locus electrical stimulation field locus.

Each of the sets of control elements 116, 118 takes the form of a double arrow (i.e., two oppositely pointing control element arrows) that can be actuated to modify the electrical stimulation field depending on the mode of operation. For example, an upper arrow control element 116a can be clicked to axially displace (i.e., along the axis of the lead 12) the locus of the electrical stimulation field in the proximal direction; a lower arrow control element 116b can be clicked to axially displace (i.e., along the axis of the lead 12) the locus of the electrical stimulation field in the distal direction; a left arrow control element 118a can be clicked to transversely displace (i.e., perpendicular to the axis of the lead 12) the locus of the electrical stimulation field in the leftward direction; and a right arrow control element 118b can be clicked to transversely displace (i.e., perpendicular to the axis of the lead 12) the locus of the electrical stimulation field in the rightward direction. The control elements 116, 118 also include indicators 116c, 118c for displaying an indication of the locus of the electrical stimulation field relative to the lead 12. In particular, an indicator 116c displays a dot representative of the axial displacement of the electrical stimulation field locus, and an indicator 118c displays a dot representative of the transverse displacement of the electrical stimulation field locus.

Figure 8A:
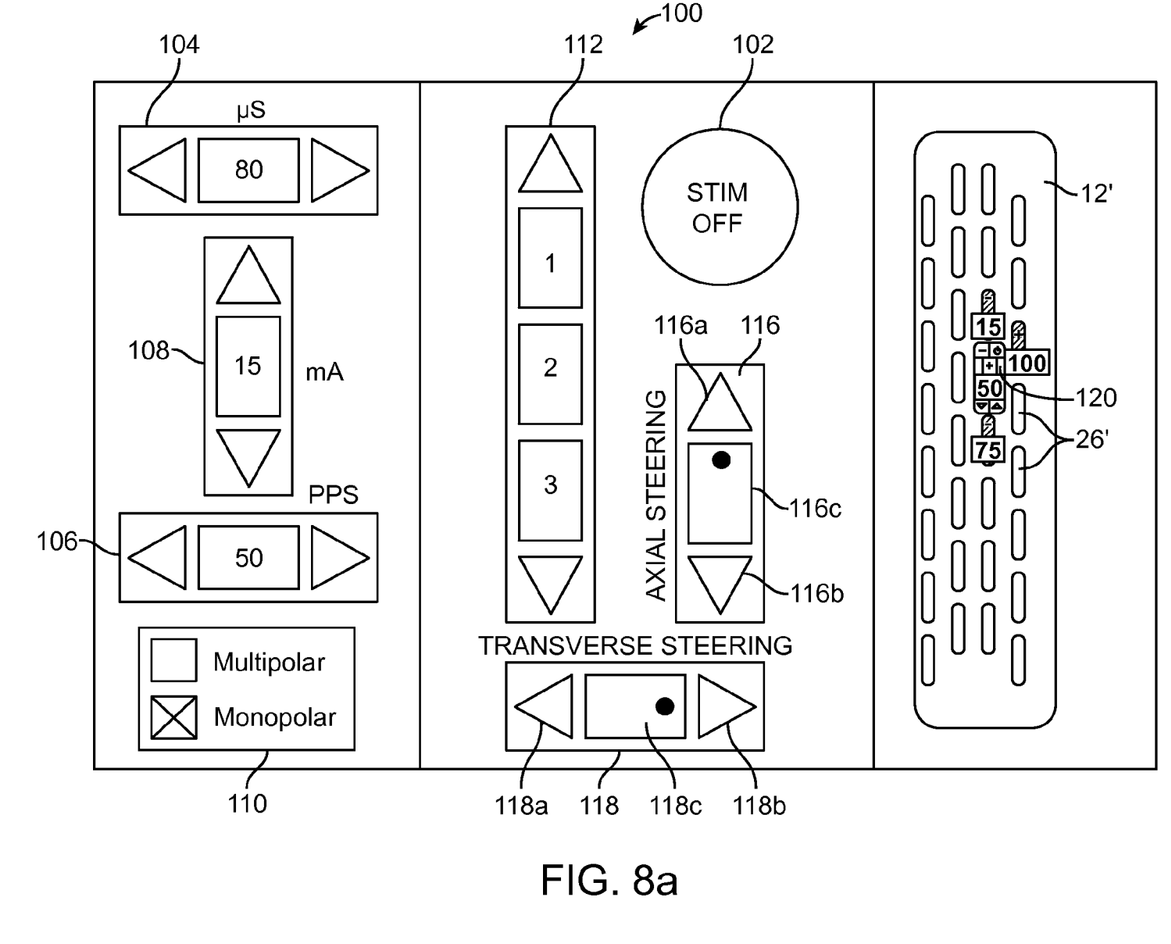
FIGS. 8a and 8b are plan views of a user interface of the CP of FIG. 7 for programming the IPG of FIGS. 3 and 4.
Figure 8B:
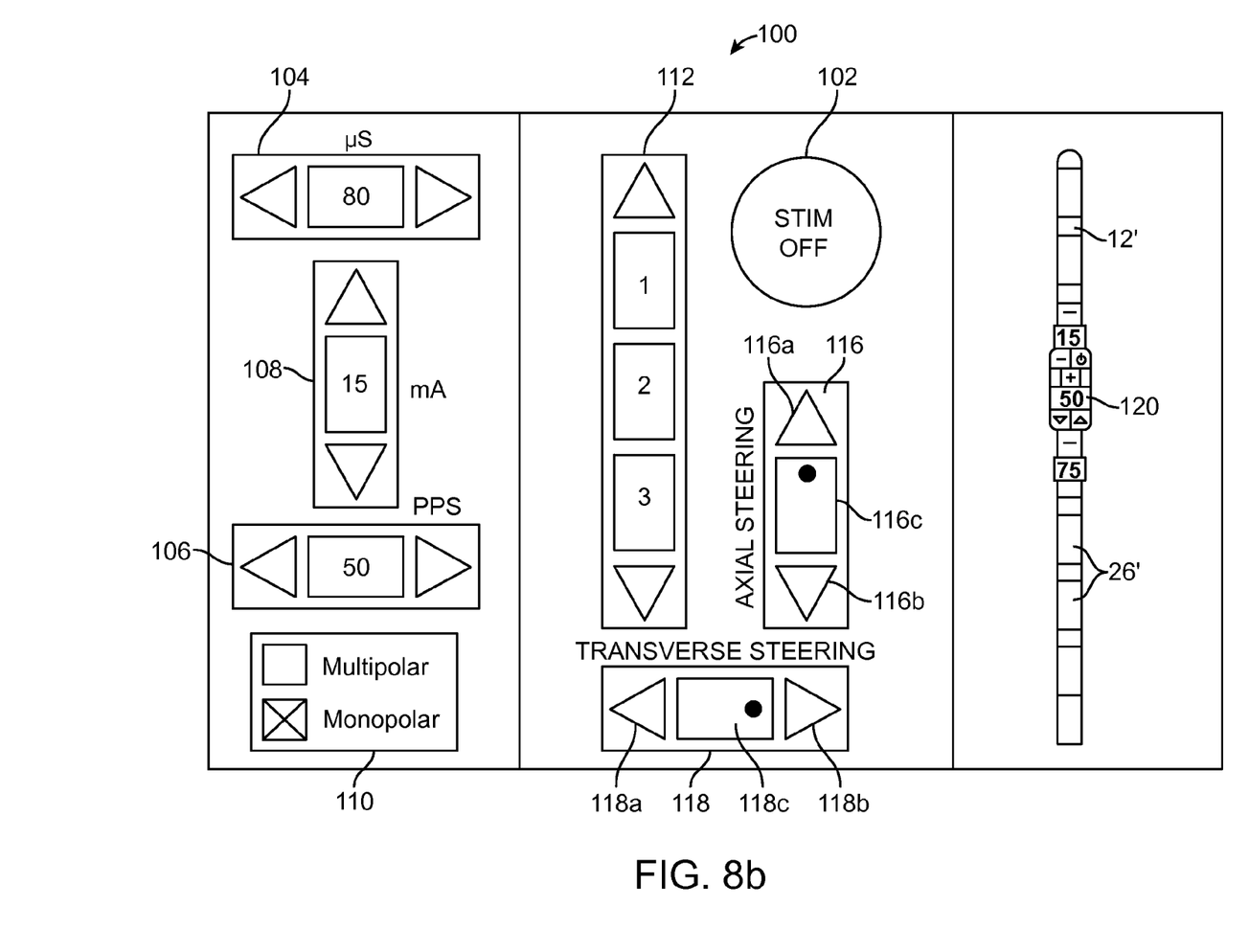

The programming screen 100 displays graphical representations of the neurostimulation leads 12' including the electrodes 26' (e.g., a graphical representation of a surgical paddle lead, as shown in FIG. 8a, or a graphical representation of a percutaneous lead, as shown in FIG. 8b). Programming information in the form of a specified stimulation amplitude value and polarity are displayed in each electrode representation 26' corresponding to an active electrode. In the illustrated embodiment, the stimulation amplitude values are fractionalized electrical current values (% current), such that the stimulation amplitude values for each polarization totals to 100. However, in alternative embodiments, the stimulation amplitude values may be normalized current or voltage values (e.g., 1-10), absolute current or voltage values (e.g., mA or V), etc. Furthermore, the stimulation amplitude values may be parameters that are a function of current or voltage, such as charge (current amplitude×pulse width) or charge injected per second (current amplitude×pulse width×rate (or period)).

Significantly, when the control element is actuated, a graphical programmer control 120 is superimposed over the graphical representation of each electrode 26'. In the illustrated embodiment, the control element is a graphical element, and in particular, takes the form of the graphical representation of the electrode 26' itself. In the illustrated embodiment, each electrode representation 26' takes the form of a closed geometric figure, and in this case a rectangle, that can be actuated using a pointing element, such as an actual pointing element (e.g., a finger or active or passive stylus) that can be used to physically tap the portion of the display screen coincident with the electrode representation 26' or otherwise brought into proximity with respect to the electrode representation 26', or a virtual pointing element (e.g., a cursor) that can be used to graphically click on the electrode representation 26'. In essence, the electrode representations 26' themselves operate as control elements, the actuation of which transforms the respective electrode representations 26' into the graphical programmer control 120.

In alternative embodiments, the control element, the actuation of which prompts the transformation of an electrode representation 26' into a graphical programmer control 120, may be a graphical control element that is separate from the respective electrode representation 26' but somehow associated with it (e.g., a graphical control element adjacent the respective electrode representation 26'), such that the user can readily identify the control element as being specific to the respective electrode representation 26'. In further alternative embodiments, the control element, the actuation of which prompts the transformation of an electrode representation 26' into a graphical programmer control 120, may not be graphical in nature; e.g., such control element can take the form of a specified key on a key board. In any event, as can be seen from FIGS. 8a and 8b, the graphical programmer control 120 does not obscure any of the other graphical electrode representations 26' or any of the programming information associated with the electrode representations 26'. In the preferred embodiment, the graphical control element 120 occupies more area on the display screen than does the electrode representation 26', and completely surrounds the electrode representation 26'.

Figure 9A:
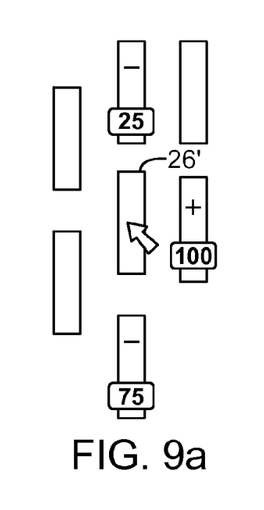
FIGS. 9a-9e are plan views respectively illustrating the use of a graphical programmer control associated with an electrode to program different polarity and stimulation amplitude values for the electrode.
Figure 9B:
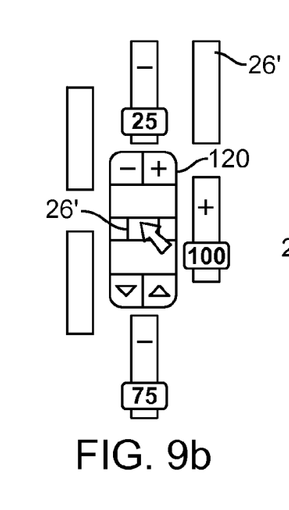

Referring to FIGS. 9a-9e, the operation of the graphical programmer control 120 will now be described. As shown in FIG. 9a, two of the electrode representations 26' have been programmed as cathodes having fractionalized electrical current values of 25% and 75%, respectively, and one of the electrode representations 26' has been programmed as an anode having a fractionalized electrical current value of 100%. The control element associated with one of the electrode representations 26' (in this case, the electrode representation 26' itself) can be actuated in the manner described above (e.g., by clicking it with a graphical cursor as shown) to transform it into a graphical programmer control 120, as shown in FIG. 9b.

In the illustrated embodiment, the graphical programmer control 120 takes the form of a box that contains various control and display elements. When any of the control elements of the graphical programmer control 120 is actuated, a stimulation parameter for the electrode 26 associated with the graphical programmer control 120 is modified, and a display element within the graphical programmer control 120 is prompted to display the status of the stimulation parameter.

Figure 9C:
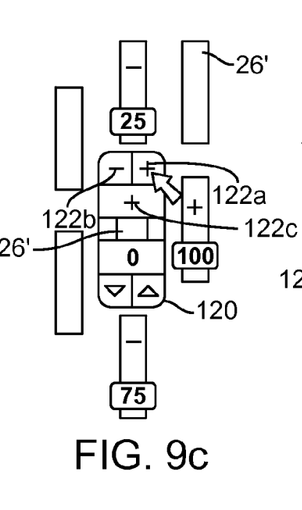

For example, the graphical programmer control 120 includes a positive polarity control element 122a (indicated with a plus-sign), the actuation of which prompts the polarity of the associated electrode 26 to be set to positive, and a negative polarity control element 122b (indicated with a minus-sign), the actuation of which prompts the polarity of the associated electrode 26 to be set to negative. A polarity display element 122c is also prompted to display the polarity status of the associated electrode 26. As shown in FIG. 9c, the positive polarity control element 122a has been actuated to program the associated electrode 26 with a positive polarity, and the display element 122c displays a plus-sign, indicating that the polarity status of the associated electrode 26 is positive. Of course, if the negative polarity control element 122b is actuated to program the associated electrode 26 with a negative polarity, the display element 122c will display a minus-sign, indicating that the polarity status of the associated electrode 26 is negative.

Figure 9D:
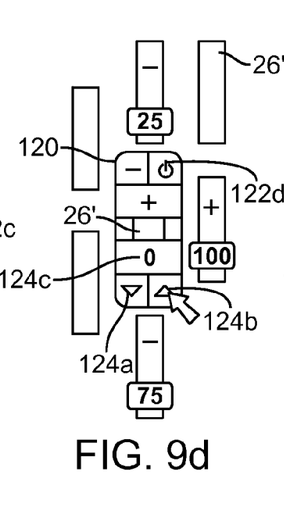

Upon actuation of one of the polarity control elements 122, the respective polarity control element 30 is transformed into a reset control element 122d, indicated by an on/off sign, as shown in FIG. 9d. If the reset control element 122d is actuated, the graphical program control 120 will be transformed back to the electrode representation 26', as shown in FIG. 9a.

Figure 9E:
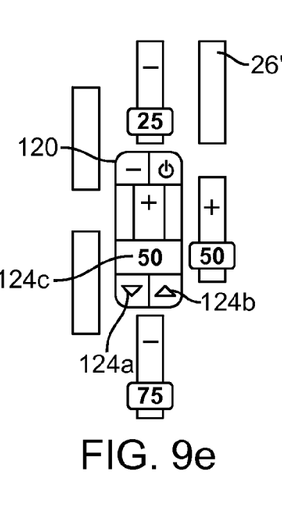

The graphical programmer control 120 further includes a stimulation amplitude control element 124a that takes the form of a down arrow, the actuation of which incrementally decreases the stimulation amplitude of the associated electrode 26, and an electrical current element 124b that takes the form of an up arrow, the actuation of which increases the stimulation amplitude of the associated electrode 26. In the case where the stimulation amplitude is a fractionalized current value, the electrical current can be adjusted in, e.g., 5% increments. A polarity display element 124c is also prompted to display the polarity status of the associated electrode 26. As shown in FIG. 9e, the stimulation amplitude control element 124b has been actuated to increase the fractionalized electrical current value from 0% to 50%, thereby programming the associated electrode 26 with a fractionalized current of 50%, as indicated by the display element 124c. In an optional embodiment, the stimulation amplitude control elements 32 are inactive, as shown grayed out in FIG. 9b, until one of the polarity control elements 30 is actuated, after which the stimulation amplitude control elements 32 become active, as shown in FIG. 9c. Although the foregoing techniques have been described as being implemented in the CP 18, it should be noted that these techniques may be alternatively or additionally implemented in the RC 16.

Although the graphical programmer control features have been described herein as being applied to the programming of electrodes using stimulation parameters, it should be appreciated that the graphical programmer control features can be applied to the programming of other types of operative elements with operational parameters, including other end effectors (i.e., operative elements that produce an effect in the patient) and sensing elements. For example, if an implantable drug pump is used, the end effector may be a catheter, and the operational parameters may be drug flow direction, drug flow rate, drug mix, etc. In the case where the operative element is a sensor, the operational parameters may include polarity, sensor grouping, sensitivity, blanking periods, input filter characteristics, etc.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for use with a programmable implantable medical device coupled to a plurality of operative elements, comprising:
   a user interface comprising at least one control element and a display screen configured for displaying graphical representations of the operative elements;
   control circuitry configured for prompting the display screen to superimpose dedicated graphical programmer controls respectively over the graphical representations of the operative elements when the at least one control element is actuated, and modifying an operational parameter for only one operative element in response to actuation of the graphical programmer control corresponding to the one operative element; and
   output circuitry configured for transmitting the modified operational parameters to the programmable implantable medical device.

2. The external control device of claim 1, wherein each of the operative elements is an end effector.

3. The external control device of claim 2, wherein each of the end effectors is an electrode.

4. The external control device of claim 3, wherein the implantable medical device is a neurostimulation device, and each of the operational parameters is a stimulation parameter.

5. The external control device of claim 4, wherein each of the graphical programmer controls comprises at least one stimulation amplitude control element, each of the stimulation parameters comprises a stimulation amplitude value for the respective electrode, and the control circuitry is configured for modifying the each stimulation amplitude value in response to actuation of the respective at least one stimulation amplitude control element.

6. The external control device of claim 5, wherein the each stimulation amplitude value is an electrical current value.

7. The external control device of claim 6, wherein the each electrical current value is a fractionalized electrical current value.

8. The external control device of claim 5, wherein the at least one stimulation amplitude control element of each graphical programmer control comprises an up arrow control element and a down arrow control element, wherein the control circuitry is configured for increasing the stimulation amplitude value in response to actuation of the respective up arrow control element, and for decreasing the stimulation amplitude value in response to actuation of the respective down arrow control element.

9. The external control device of claim 4, wherein each of the graphical programmer controls further comprises at least one polarity control element, each of the stimulation parameters comprises a polarity for the electrode, and the control circuitry is configured for modifying the polarity in response to actuation of the respective at least one polarity control element.

10. The external control device of claim 9, wherein the at least one polarity control element of each graphical programmer control comprises a positive polarity control element and a negative polarity control element, wherein the control circuitry is configured for setting the polarity of the electrode to a positive polarity in response to actuation of the respective positive polarity control element, and for setting the polarity of the electrode to a negative polarity in response to actuation of the respective negative polarity control element.

11. The external control device of claim 1, wherein the user interface further comprises a display element incorporated within each of the graphical programmer controls, and wherein the control circuitry is further configured for prompting the each display element to display a status of the respective modified operational element.

12. The external control device of claim 1, wherein each of the at least one control element is a graphical control element.

13. The external control device of claim 12, wherein each of the at least one graphical control element is the graphical representation of the respective operative element.

14. The external control device of claim 13, wherein each of the graphical programmer controls occupies more area on the display screen than does the graphical representation of the respective operative element.

15. The external control device of claim 1, wherein each of the graphical programmer controls surrounds the graphical representation of the respective operative element.

16. The external control device of claim 1, wherein the display screen is configured for displaying graphical representations of the other operative elements, and the graphical programmer controls do not obscure any of the graphical representations of the operative elements.

17. The external control device of claim 16, wherein the display screen is configured for displaying programming information within the graphical representations of the operative elements, and the graphical programmer controls do not obscure any of the programming information.

18. The external control device of claim 1, wherein the output circuitry comprises telemetry circuitry.

19. The external control device of claim 1, further comprising a case containing the user interface, control circuitry, and output circuitry.

* * * * *